United States Patent [19]

Slepak et al.

[11] 4,201,080

[45] May 6, 1980

[54] MOISTURE INDICATOR

[75] Inventors: Bernard Slepak, 252 Greenbay Rd., Highland Park, Ill. 60035; John E. Tucker, Cincinnati, Ohio; William P. Heinrich, McHenry, Ill.

[73] Assignee: Bernard Slepak, Chicago, Ill.

[21] Appl. No.: 906,942

[22] Filed: May 18, 1978

Related U.S. Application Data

[63] Continuation of Ser. No. 744,738, Nov. 24, 1976, abandoned.

[51] Int. Cl.$^2$ ............................................. G01N 25/56
[52] U.S. Cl. ....................................... 73/73; 116/206
[58] Field of Search ............ 73/73; 116/114 AM, 206; 252/408 R

[56] References Cited

U.S. PATENT DOCUMENTS

| | | | |
|---|---|---|---|
| 2,446,361 | 8/1948 | Clibbon | 312/31.1 |
| 2,460,073 | 1/1949 | Davis | 252/408 |
| 2,460,074 | 1/1949 | Davis | 252/408 |
| 2,520,993 | 9/1950 | Berger | 252/408 |
| 2,614,650 | 10/1952 | Chandler et al. | 55/275 |
| 2,716,338 | 8/1955 | Blinn | 73/73 |
| 2,787,238 | 4/1957 | Luce | 116/114 AM |
| 3,019,638 | 2/1962 | Klein | 73/73 |
| 3,026,718 | 3/1962 | Matson | 73/73 |
| 3,260,234 | 7/1966 | Serrano et al. | 116/114 R |
| 3,408,860 | 11/1968 | Knieriem et al. | 73/73 |
| 3,680,364 | 8/1972 | Carrier | 73/73 |
| 3,951,098 | 4/1976 | Meyers | 73/73 |

Primary Examiner—Anthony V. Ciarlante
Attorney, Agent, or Firm—Henry L. Brinks; Joan I. Norek

[57] ABSTRACT

A moisture indicator is provided suitable for use in determining the wet-dry cycle of the soil surrounding cultivated plants. The soil moisture indicator comprises an upper and lower chamber with an interconnecting passageway across which is positioned an absorbent supporting material impregnated with a moisture sensitive indicator composition. The lower chamber has a bottom opening which upon insertion into the soil results in the relative humidity in the lower chamber being related to the wetness of the soil. The upper chamber is partially transparent and may optionally be vented to the outer atmosphere.

17 Claims, 4 Drawing Figures

U.S. Patent May 6, 1980 4,201,080
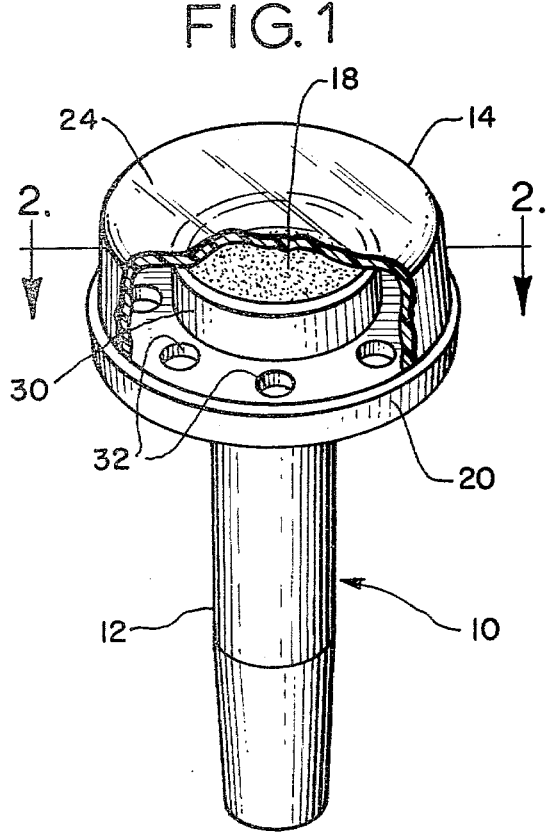
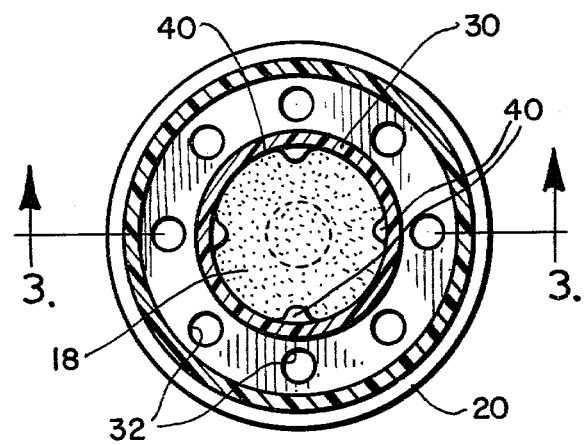
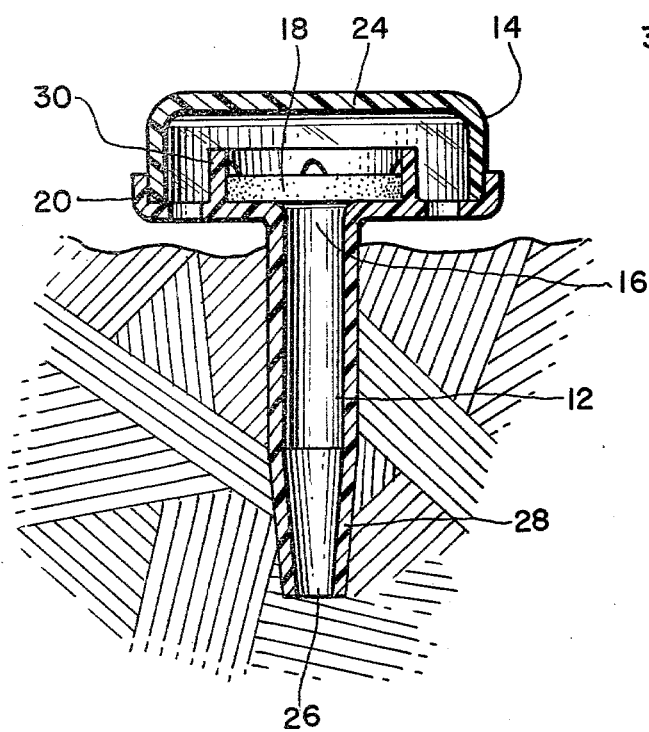
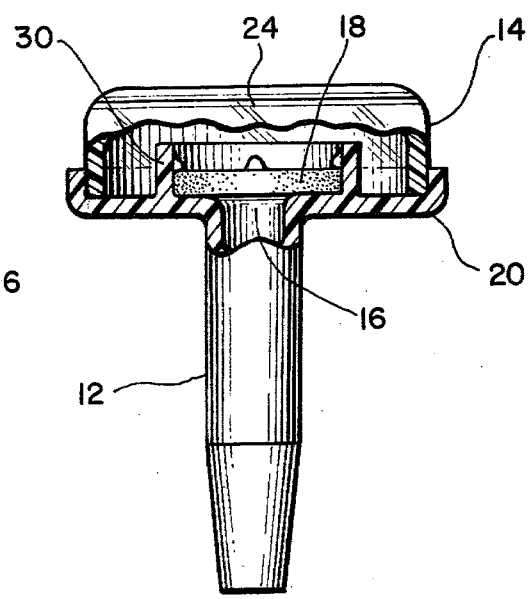

MOISTURE INDICATOR

This is a continuation of application Ser. No. 744,738, filed Nov. 24, 1976 now abandoned.

BACKGROUND OF THE INVENTION

Proper care of cultivated plants requires adequate watering without overwatering. Watering is essential not only for plants grown indoors but also in many cases to supplement rain water for plants grown out of doors. If a plant however receives too much water, root rot may develop, resulting in deterioration and even the death of the plant.

Overwatering a plant with too much water at one time can easily be guarded against by providing proper drainage such as drainage holes for indoor plants. Such drainage holes allow excess water, that is water not absorbed by the soil, to seep away from the soil and root growing area of the plant. Pots with such drainage holes usually have outer containers which collect such water. Alternatively, drainage can be accomplished by placing a layer of rocks or other such material in the bottom of a pot below the soil.

A plant which is provided with proper drainage such as by the above methods or a plant being cultivated in the ground can still suffer from overwatering, not by receiving too much water at one time but by receiving water too often. It is therefore usually recommended by plant growing experts that the soil in which a plant is potted be allowed to dry thoroughly between waterings. This is the general rule of thumb for the majority of cultivated plants. There are exceptions, such as succulents which are maintained for long periods in substantially dry conditions or ferns which usually are maintained in constantly moist soil. Most plants however thrive best when they receive a thorough watering shortly after being allowed to dry.

The appropriate time interval between waterings, hereinafter referred to as the wet-dry soil cycle, varies with many factors. It will vary with the characteristics of the individual plant, the amount of water taken up by the plant's root being dependent not only upon its age but also upon the time of year. Most plants go through a period of reduced water need during the winter season. Another factor is the composition of the soil surrounding the roots. Different soils retain different amounts of water. Environmental conditions also can vary the wet-dry cycle by affecting the rate of water evaporation from the soil. These environmental conditions include such factors as temperature and humidity of the atmosphere.

Determination of the appropriate watering time of any particular plant requires either or both observation of the plant or testing the moisture content of the soil. The leaves of a plant often will droop when the plant is in need of water. Overwatering a plant however may also cause droopage of the leaves. Relying on observation of the plant itself to determine the appropriate time for watering is therefore not practical especially for those persons without extensive experience in plant cultivation.

The second method of determining a plant's water needs, testing the soil by touching the upper surface, can also lead to unreliable results because the upper layer has a tendency to dry more quickly than the lower layers due to evaporation from the surface. Testing the soil below the very upper surface is therefore the most preferred method of determining soil moisture. This type of testing by hand requires disturbing the soil repeatedly and can be unduly time consuming when the method needs to be performed on a multitude of plants.

Devices for determining the moisture content of soil below the immediate upper surface by visual observation have been known, but suffer from serious drawbacks for use in the home or in the office or in the garden. These known devices can be considered in two categories. The first category includes sophisticated moisture gauges, such as those disclosed in U.S. Pat. No. 2,801,538, U.S. Pat. No. 2,878,671, U.S. Pat. No. 3,026,718 and U.S. Pat. No. 3,045,477. These moisture gauge indicators determine soil moisture by measuring such variables as osmotic pressure. These are sensitive instruments and although apparently durable, they are too costly to be practical for casual use in the home or garden.

The second category of indicators includes devices such as that disclosed in U.S. Pat. No. 3,824,844, which are inexpensive and generally use a hydrophyllic material covered by a layer of plastic in which a hole is pierced thereby providing soil moisture access to a small portion of the hydrophyllic material. These devices, when placed partially within the soil surrounding a plant, result in the moisture content of the hydrophyllic material being proportional to the moisture content of the soil. The hydrophyllic material or a portion thereof is chemically treated so that it changes color with a change of moisture content. Visual observation of the color of this material is indicative of soil moisture. These devices, wherein a portion of the hydrophyllic material is exposed directly to organisms contained in the soil, are subject to deterioration presumably by organisms contained in the soil. These devices have also been found to react slowly to moisture changes.

SUMMARY OF THE INVENTION

The present invention provides a moisture indicator which is particularly suitable for use in determining the wet-dry cycle of both indoor and outdoor potted plants and for garden plants. The present invention provides a soil moisture indicator that is inexpensive to manufacture and yet not subject to deterioration caused by direct contact of the moisture indicating material with the soil. The present invention further provides an indicator which is simple to install and is easy to read by casual visual observation. The present invention further provides a soil moisture indicator which is reliable over an extended period of time and accurately reflects a plant's water needs.

The present invention utilizes an absorbent material chemically treated so as to adequately change colors with moisture content. Such material is conveniently a sheet of water-absorbing support material impregnated with a composition containing, for example, cobalt chloride which when subject to a moist atmosphere appears pink in color and which when subject to a low moisture atmosphere appears blue in color. The use of cobalt compounds as moisture indicators is well known in the art, for example as discussed in U.S. Pat. No. 2,460,071, U.S. Pat. No. 2,460,073, U.S. Pat. No. 2,580,737, and U.S. Pat. No. 3,246,758. The amount of cobalt compound contained in the absorbent material and the presence of other chemicals can effect the sensitivity to moisture regarding not only the amount of moisture that will affect a color change but also the time in which the color change is effected. The particular composition of the indicator material utilized in the present invention is therefore a further feature of the present invention.

It is important to the present invention that the indicator utilized does not turn pink, indicating the wet stage of the wet-dry cycle until the plant soil is thoroughly watered. Therefore, in a preferred embodiment of the present invention an agent is also incorporated into the indicator paper which raises the humidity level at which the indicator changes color.

The general object of the present invention is to provide an inexpensive and accurate soil moisture indicator which is not only simple and practical to use but is not subject to deterioration from organisms within the soil.

Other objects of the invention will become apparent upon consideration of the following description and the appended drawings.

SUMMARY OF DRAWINGS

FIG. 1 is an elevational view of a moisture indicator embodying the present invention;

FIG. 2 is a cross-sectional view of the moisture indicator of FIG. 1, along lines 2—2;

FIG. 3 is a cross-sectional view of the moisture indicator along lines 3—3; and

FIG. 4 is a partially cut away side view of a further moisture indicator embodying the present invention.

DESCRIPTION OF THE PREFERRED EMBODIMENTS

With reference to the drawings, there is shown, as an example of one form in which the present invention may be embodied, a moisture indicator generally designated by the numeral 10 in FIG. 1. The indicator includes a lower chamber 12 which is substantially cylindrical and supports an upper chamber 14. A passage 16 interconnecting said lower and said upper chambers as best seen in FIGS. 3 and 4, is entirely covered by a membrane 18 whereby moisture communicating between the chambers 12, 14 substantially traverse the membrane 18. The membrane 18 contains a moisture indicator composition which changes color responsive to the humidity of the lower chamber. The upper chamber as shown in FIGS. 1 to 4 is defined by a supporting collar 20 and a cap 24 whose outer perimeter is of such dimensions that it fits snugly within the sides of the collar 20.

Further as shown in FIGS. 1, 3 and 4, a retaining wall 30 is also supported by the collar and surrounds the indicator material 18 restraining it from sideward movement.

The collar 20, the sheet of membrane 18, and the membrane retaining wall 30, are all illustrated as being of a circular shape. It is of course obvious that other shapes could be utilized and still fall within the scope of the present invention, such as squares or diamonds or fanciful patterns. The relationship of the shape of the retaining wall to the shape of the layer of membrane need only be such that the material is effectively retained. Nor need be the retaining wall 30 be a continuous wall. Suitable notches or flanges which would prevent sideward movement or any other retaining means could be utilized. The shape and configuration of the body defining the chamber 14 in which the membrane is placed is shown in FIG. 1 for its simplicity. The symmetry of the device as shown in FIG. 1 however also facilitates the air movement and is therefore a preferred embodiment of the present invention.

The absorbent membrane 18, according to the present invention, is disposed above the surface of the soil and protected from contact therewith by being contained in an upper chamber 14, which chamber is at least partially transparent. The absorbent membrane is positioned so that a portion thereof extends across an opening 16 in the lower surface of the upper chamber. This opening 16 interconnects the upper chamber 14 to a lower chamber 12 which can be in the form of an axial cavity 12 of a stem portion of the device.

The present invention can be broadly described as two chambers interconnected by a passage, which passage is substantially covered by absorbent membrane supporting an indicator composition. The upper chamber 14 is partially transparent so as to facilitate viewing the indicator material. In a preferred embodiment of the present invention, the upper chamber 14 is vented to the outside atmosphere such as by vents 32. The lower chamber is provided with a bottom opening 26 for insertion in the soil, the moisture content of which is to be tested at a point below the upper surface of the soil.

The lower chamber 12 can be substantially in the form of a cylinder or stem which supports the upper chamber 14 and, due to the cylindrical shape of the stem, is easily inserted or removed from the soil. The lower chamber in the stem has a smaller cross-sectional area 12 across the flow path than the upper chamber.

The stem portion 12 of the device 10 is inserted along a substantial portion of its length into the soil. The stem portion 12, supporting the upper chamber, provides an interconnection between said indicator material and the soil at a depth below the upper surface of the soil. The indicator material 18 separates, and is in contact with the air in, both the upper and lower chambers. The air contained in this stem or lower chamber 12 therefore tends toward equilibrium with the moisture content of the soil below the top surface of the soil and the moisture content, or humidity, of the air in the stem is therefore varied as a function of the moisture content of the subsurface soil.

The upper chamber may be enclosed to avoid sensitivity of the indicator material to the humidity of the surrounding environment. It has been found, surprisingly, however, that providing outlets or vents 32 between the upper chamber and the outer atmosphere, such as a series of holes in the bottom of the upper chamber, results in increased sensitivity of the indicator material to changes in the moisture content of the soil. A moisture indicator with an upper chamber vented to the atmosphere and a lower chamber opened to subsurface soil and indicator material interconnecting such chambers comprises a further preferred embodiment of the present invention.

As mentioned above, the composition of the indicator material impregnated into the membrane 18 is a feature of the present invention. The indicator material of the present invention is not in direct contact with the soil whose moisture content is to be determined by the invention. One side of the indicator material is in contact with the air in the lower chamber and the humidity thereof is the variable to which the indicator material responds.

The membrane 18 has a moisture absorbent base, such as absorbent paper. Blotting papers suitable for such use are well known in the art.

Such paper is impregnated with moisture indicator composition, such as cobalt chloride, which produces a visible color change when exposed to a particular relative humidity. The absorbent membrane absorbs an amount of water which varies with the relative humidity of the environment which acts upon the indicator or composition to cause the visible color change.

The color change of cobalt chloride is resultant from an equilibrium reaction such as:

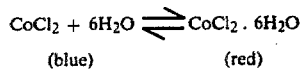

$$CoCl_2 + 6H_2O \rightleftharpoons CoCl_2 \cdot 6H_2O$$
(blue) (red)

Cobalt chloride indicator generally is blue when exposed to atmospheric relative humidity up to about 55%; above 55% it turns pink. The time required for the color change of the indicator upon exposure to a relative humidity that will effectuate a change is dependent upon, among other variables, the humidity. That is, an indicator composition containing cobalt chloride will change from blue to pink faster when exposed to a relative humidity of 90% as compared to 70%, although exposure to either will eventually effectuate the change.

The upper cap 24 in FIG. 1 is illustrated as being entirely transparent, providing a view of any color changes of membrane 18 from a variety of angles.

The supporting collar 20 of the upper chamber is shown in FIGS. 1, 2 and 3 to contain appertures or vents 32 providing a chamber that is therefore open to the atmosphere. Placement of these appertures in the lower wall of the upper chamber, the supporting collar 20, is shown, but location of such vents elsewhere is contemplated by the present invention.

As best shown in FIG. 2, the retaining wall 30 for the membrane 18 is provided with notches 40 along its inner circumference. The notches 40 restrain the membrane from an upward movement preventing accidental dislodgement.

FIG. 3 shows most clearly the positioning of the membrane 18 above the substantially centered passage 16 interconnecting the upper chamber 14 and the lower chamber 12 forming a passageway from the upper chamber to the opening 26 in the lower chamber. As shown most clearly in FIG. 3, the lower chamber 12 has preferably an inward tapered lower portion or joint 28 which facilitates placement of the indicator in the soil and provides additional support for said indicator.

FIG. 3 also illustrates the preferred positioning of the indicator device in the soil, that is, positioning so that the upper chamber 14 is disposed approximately 1/16 to ¼ of an inch above the surface of the soil.

The indicator device illustrated in FIG. 4 is substantially the same as illustrated in FIGS. 1 to 3 except that there are no vents 32 between the upper chamber and the surrounding atmosphere.

The membrane 18 may be a sheet of blotting paper or other absorbent material which is impregnated with the indicator composition. A preferred method for impregnating the membrane is to immerse the membrane into a solution containing the composition. An aqueous solution may be used but the solvent, which is thereafter evaporated from the material, of course will be chosen based on solubilities of the composition.

The indicator composition employed in the present invention comprises cobalt chloride. Preferably, however, the cobalt chloride is used in combination with an agent that provides a color change in the relative humidity range from about 80% to 90%, for example, cobalt chloride in combination with a thiocyanate salt such as potassium thiocyanate. Inclusion of other anions and cations by adding salts to enchance the color, such as sodium and calcium chloride is contemplated.

Other methods of saturating the absorbent material with solutions containing the above described chemicals and thereafter removing the solvent are well known in the art and the present invention is not limited to any particular of preparing the indicator composition.

The preferred indicator composition is best expressed in terms of proposition by weight of the cobalt chloride to thiocyanate salt. The present invention contemplates the use of a composition including cobalt chloride and potassium thiocyanate preferably at a weight ratio range of 1:0.5 to 1:0.8. A weight proposition of 1:0.6 to 1:0.7 of cobalt chloride to potassium thiocyanate is a more preferred embodiment of the invention. Of course, an equivalent amount of other thiocyanate salts may be substituted for the potassium thiocyanate such as sodium or calcium salts.

The invention is further illustrated by the following example which discloses impregnation of the blotting paper with the indicator composition.

EXAMPLE

Suitable indicator material was prepared by immersing a blotting paper in a solution of 28 grams of cobalt chloride, 15 grams sodium chloride, 4 grams calcium chloride (anhydrous), and 19 grams potassium thiocyanate, diluted to a total solution volume of 380 milliliters with water. The paper was immersed so that the solution covered both sides of the paper. The paper was then hung to air dry.

Although the exact mode of operation of the present invention is not completely understood it is believed that the moisture content of the air with the lower chamber defined by the stem varies as a function of the moisture content of the soil. The indicator composition, exposed to both the atmosphere of the upper and lower chambers on the membrane 18, is responsive to the highest humidity. Accordingly, if the humidity on one side of the paper is for example 90% and on the other side below 55%, the paper will respond to the highest humidity and, if it contains cobalt chloride, will turn pink. This theory provides an explanation for the superior results obtained in the embodiment of the present invention wherein the upper chamber is vented to the outer atmosphere. When the plant soil is watered the humidity in such lower chamber is above 70 to 80% and turn the indicator material pink. When the soil dries out, the humidity in the lower chamber drops. The vents in the upper chamber permit the paper to "dry out." The vents permit the paper to track the soil condition more quickly since the paper will evaporate moisture to the atmosphere. In other words, the vents tend to keep the paper at the correct moisture level by evaporating any moisture in the paper above the moisture level in the chamber. When the humidity level in the chamber drops below a certain level, for example 70%, the paper turns blue. The indicator composition does not indicate a wet condition when the atmosphere is less than about 50% to 65% relative humidity, and therefore is unaffected by normal room humidity.

We claim:
1. A soil moisture indicator comprising:
a first chamber;
a second chamber;

said second chamber having a bottom opening for communication with the subsurface of the soil;

passage means interconnecting said first chamber and said second chamber;

a moisture indicator composition having a color change response to a relative humidity in said second chamber at a point above at least about 70%;

a moisture indicator support material positioned across said passage means interconnecting said first and said second chambers, said material separating said first and second chambers and supporting said indicator composition, whereby sufficient portions of air containing moisture communicating between said first and said second chamber traverse said moisture indicator support material to provide moisture indicating color change;

said first chamber defining an air chamber provided with a transparent portion for viewing the color response of the indicator composition; and wherein said second chamber is formed as an elongated stem, said bottom opening being formed in the lower portion of the bottom of said stem and said passage means being disposed opposite said bottom opening, said second chamber supporting said first chamber when said second chamber is in communication with the subsurface of soil through said bottom opening.

2. Said moisture indicator of claim 1 wherein said moisture indicator support material is a blotting paper treated with an aqueous solution containing cobalt chloride.

3. The moisture indicator of claim 1 wherein the indicator composition comprises cobalt chloride and a salt selected from the group consisting of sodium thiocyanate, potassium thiocyanate and calcium thiocyanate.

4. The moisture indicator of claim 3 wherein the indicator composition comprises cobalt chloride and one of said thiocyanate salts at a weight ratio range of 1:0.5 to 1:0.8 based on potassium thiocyanate.

5. A soil moisture indicator comprising:
an upper chamber vented to the outer atmosphere, said chamber composed at least partially of transparent material;
a lower soil chamber having a bottom opening for communication with the subsurface of the soil, said upper and said lower chamber being interconnected by an air flow passageway;
a member traversing the air flow passageway from said lower chamber to said upper chamber, and separating said upper and lower chambers whereby sufficient portions of the moisture communicating between said upper and lower chambers traverse said member to provide moisture indication color change; and
a moisture indicator composition having a color change responsive to a relative humidity at a point of at least about 70%, said indicator composition supported on said member.

6. The moisture indicator of claim 5 wherein said member is a blotting paper and said indicator composition comprises cobalt chloride.

7. The moisture indicator of claim 6 wherein said indicator composition further contains a salt selected from the group consisting of sodium thiocyanate, potassium thiocyanate and calcium thiocyanate.

8. The moisture indicator of claim 5 wherein said upper and lower chambers are symmetrical.

9. The moisture indicator of claim 8 wherein said stem portion of said lower chamber is substantially cylindrical and tapering about its lower end.

10. A soil moisture indicator comprising:
an upper chamber, said upper chamber being defined by a supporting collar and a cap of transparent material positioned upon said collar, said upper chamber containing vents to the outer atmosphere;
a lower chamber, said lower chamber being provided with a stem portion having a bottom opening for communication with the subsurface of the soil;
passageway means interconnecting said upper chamber and said lower chamber;
a membrane positioned across said interconnecting means of said chambers, and separating said upper and lower chambers whereby substantial portions of moisture communicating between said upper and said lower chamber traverse said membrane; and
an indicator composition contained on said membrane having a color change responsive to a relative humidity above about 70%.

11. The soil moisture indicator of claim 10 wherein said indicator composition has a color change responsive to a relative humidity in said lower chamber in the range from about 80% to 90%.

12. The soil moisture indicator of claim 10 wherein said indicator composition comprises cobalt chloride and a thiocyanate salt selected from the class consisting of sodium thiocyanate, potassium thiocyanate, and calcium thiocyanate.

13. The soil moisture indicator of claim 12 which further includes notches on the inner surface of the retaining wall which are positioned above the indicator material so as to prevent upward movement of said indicator material.

14. The moisture indicator of claim 10 wherein said membrane is blotting paper and said indicator composition is cobalt chloride.

15. The moisture indicator of claim 10 wherein said membrane is blotting paper and said indicator composition comprises cobalt chloride and a salt selected from the group of sodium thiocyanate, potassium thiocyanate and calcium thiocyanate.

16. The moisture indicator of claim 10 wherein said membrane is a blotting paper containing an indicator composition prepared by treating said paper with an aqueous solution of cobalt chloride and a thiocyanate salt.

17. The moisture indicator of claim 10 wherein said membrane is a blotting paper containing an indicator composition prepared by treating said blotting paper with an aqueous solution of cobalt chloride containing a salt selected from the group of sodium thiocyanate, potassium thiocyanate and calcium thiocyanate at a weight ratio of cobalt chloride to thiocyanate salt of 1:0.6 to 1:0.7 based on potassium thiocyanate.

* * * * *